United States Patent [19]

Rohrbacker et al.

[11] Patent Number: 5,395,501

[45] Date of Patent: Mar. 7, 1995

[54] GAS GENERATING APPARATUS

[75] Inventors: David A. Rohrbacker, Tucson, Ariz.; John R. Finbow, Southampton, England

[73] Assignees: City Technology Ltd.; Advanced Calibration Designs, Inc., Tucson, Ariz.

[21] Appl. No.: 192,256

[22] Filed: Feb. 7, 1994

[30] Foreign Application Priority Data

Feb. 12, 1993 [GB] United Kingdom ............ 9302838

[51] Int. Cl.⁶ .................... C25B 9/00; C25B 15/08
[52] U.S. Cl. .................... 204/265; 204/266
[58] Field of Search ............ 204/265, 266, 256, 258

[56] References Cited

U.S. PATENT DOCUMENTS

| | | | |
|---|---|---|---|
| 3,078,218 | 2/1963 | Sundermeyer | 204/266 X |
| 3,910,831 | 10/1975 | Helart | 204/266 X |
| 4,040,936 | 8/1977 | Orth | 204/271 |
| 4,151,739 | 5/1979 | Breyer | 73/1 G |
| 4,332,664 | 6/1982 | Noszticzius et al. | 204/266 |
| 4,460,448 | 7/1984 | Wolcott | 204/266 |
| 4,786,391 | 11/1988 | Clemens | 204/266 X |
| 5,141,617 | 8/1992 | Nagy et al. | 204/266 X |

FOREIGN PATENT DOCUMENTS 3013711 10/1981 Germany.
3939166 5/1991 Germany.

*Primary Examiner*—Donald R. Valentine
*Attorney, Agent, or Firm*—Lee, Mann, Smith, McWilliams, Sweeney & Ohlson

[57] ABSTRACT

Gas generating apparatus comprises an electrochemical cell having gas generating (2) and counter electrodes (3) with an intervening body of electrolyte (9). Current passing between the electrodes causes the generation of gas at the gas generating electrode. A first membrane (24) permeable to gas but substantially impermeable to the electrolyte is positioned sufficiently close to the gas generating electrode (2) that gas generated by the gas generating electrode diffuses through the electrolyte and out through the membrane under the influence of a gas concentration gradient, substantially without forming bubbles in the electrolyte and irrespective of the orientation of the apparatus.

9 Claims, 2 Drawing Sheets

GAS GENERATING APPARATUS

FIELD OF THE INVENTION

The invention relates to gas generating apparatus comprising an electrochemical cell having gas generating and counter electrodes with an intervening body of electrolyte, whereby current passing between the electrodes causes the generation of gas at the gas generating electrode. Such apparatus is hereinafter referred to as of the kind described.

DESCRIPTION OF THE PRIOR ART

Gas generating apparatus of the kind described finds particular use in calibration gas generators. These generators are used to produce a closely controlled concentration of a gas, such as chlorine, in a purge gas for use in calibrating gas sensors. A typical example is described in U.S. Pat. No. 4,460,448.

Another typical electrochemical calibration gas generator is produced by Bedfont Technical Instruments Limited, model EC3. In this generator, chlorine gas evolves at a generating electrode immersed in an acidic electrolyte solution of potassium chloride. Purge gas is bubbled through the electrolyte chamber, mixes with bubbles of chlorine gas and vents through the top of the apparatus. Hydrogen gas evolves at a counter electrode in a second arm of the electrolyte chamber and also vents through the top of the apparatus.

A problem with this type of apparatus is that it may only be operated in one orientation since gas can only vent in one direction. Also, if the apparatus is inverted or otherwise tilted from its normal operation, electrolyte can leak out. For this reason, the generator is not particularly portable. DE-A-3013711 describes a generator which is designed to prevent electrolyte flooding during inadvertent inversion but this design does not ensure that the cell can operate in any orientation because there is no provision for the management of the bubbles which inevitably form during operation.

SUMMARY OF THE INVENTION

In accordance with the present invention, gas generating apparatus of the kind described further comprises a membrane permeable to gas but substantially impermeable to the electrolyte is positioned sufficiently close to the gas generating electrode that gas generated by the gas generating electrode diffuses through the electrolyte and out through the membrane under the influence of a gas concentration gradient, substantially without forming bubbles in the electrolyte and irrespective of the orientation of the apparatus, and wherein the electrochemical cell defines a generally U-shaped electrolyte chamber, the counter electrode extending into one of the arms of the U and the gas generating electrode being positioned at the base of the U.

With this invention, a gas generator is provided which can generate a supply of gas irrespective of its orientation since any bubbles produced by the counter electrode are prevented from interrupting electrolyte contact between the two electrodes in any orientation of the apparatus.

In some cases, any bubbles formed can be periodically vented by opening a normally closed port or the like. Preferably, the walls of the apparatus defining the chamber holding the electrolyte are at least partly formed of a second membrane permeable to gas but substantially impermeable to electrolyte arranged such that gas generated by the counter electrode can vent through the walls of the apparatus. Typically, the size of the second membrane will be such that any gas bubbles formed by the counter electrode will always be in contact with the membrane and thus will always vent to ambient atmosphere.

Preferably, the first membrane is supported by a relatively highly porous support member. The support member may comprise a web of a support structure, the web having a number of apertures extending through it or alternatively could be provided by a relatively rigid, porous member such as Vyon or Reticulated Vitreous Carbon (RVC).

An inner wall of the chamber defining the arm of the U containing the counter electrode is preferably angled towards the base of the U so as to encourage the passage of gas into the other arm when the apparatus is tilted.

The gap between the first membrane and the gas generating electrode should, as explained above, be sufficiently small that there is substantially no bubble formation but the gap should be large enough to maintain Faraday efficiency. A typical minimum gap size is 70 $\mu$m, preferably 76 $\mu$m.

The gas generating apparatus is particularly useful in a calibration gas generating system in which gas passing through the first membrane from the gas generating electrode passes into a purge gas chamber through which purge gas is passing. This arrangement is different from previous arrangements in that the purge gas was passed through the electrolyte. The new approach leads to more efficient mixing of the gases in the purge chamber and better control of the gas concentrations.

BRIEF DESCRIPTION OF THE DRAWINGS

An example of a calibration gas generating system according to the invention will now be described with reference to the accompanying drawings, in which.

DETAILED DESCRIPTION OF AN EMBODIMENT

Figure 2:
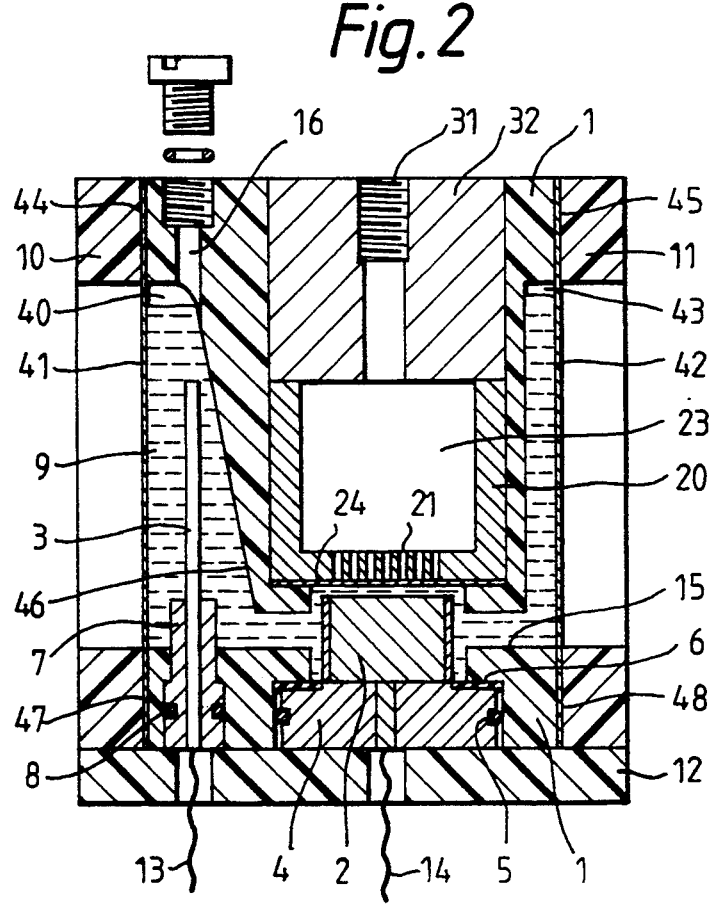
FIG. 2 is a cross-section along the line A—A in FIG. 1.

As shown in FIG. 2, the gas generator consists of a plastics housing 1, including apertures for holding a generating electrode 2, and a counter electrode 3. The generating electrode 2 shown in FIG. 2 is fixed in an electrode support 4. The support is fixed by a plastics clamp plate 12, and contacts the housing 1 via an O-ring 5 and PTFE sealing gasket 6. The counter electrode is held by a support 7, with an O-ring 8. Both electrodes are connected to a current source (not shown) by wires 13,14.

Electrolyte fluid 9 is contained in an electrolyte chamber formed between the housing 1, and plastics side plates 10 and 11 carrying semi-permeable membranes 41, 42 which contain the electrolyte but are permeable to gas. The electrolyte chamber is filled via port 16.

Figure 3:
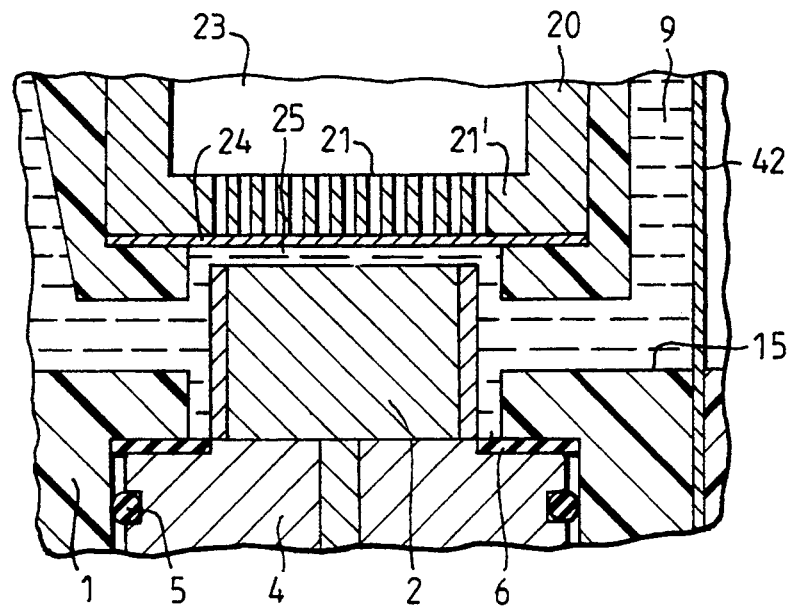
FIG. 3 is an enlarged view of a portion of FIG. 2.

A purge gas chamber block 20 defining a purge gas chamber 23 is fixed above the generating electrode 2, separated by a gap 25 containing electrolyte, and PTFE membrane 24 (as shown in FIG. 3) which prevents loss of electrolyte.

Figure 4:
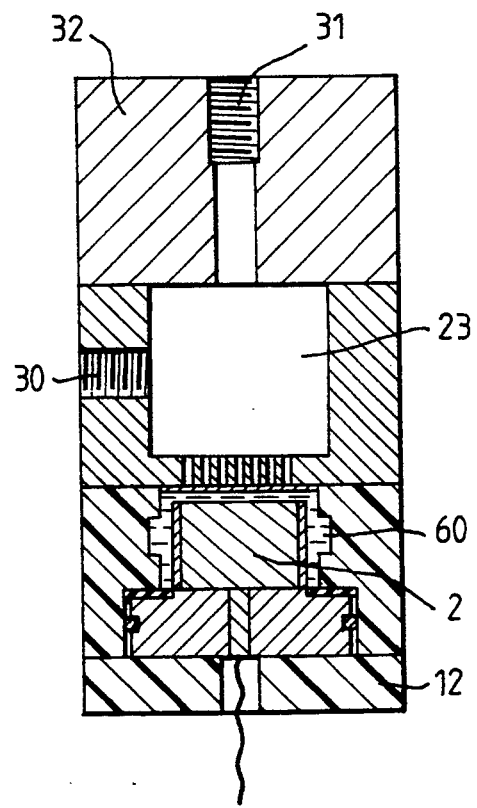
FIG. 4 is a cross-section orthogonal to the line A—A.

In use, gas is generated at the generating electrode 2, diffuses across the gap 25 due to the concentration gradient and without the formation of bubbles, through the semi-permeable membrane 24, and into the purge gas chamber 23 via a grid of holes 21. The grid of holes 21 is formed in a base 21' of the block 20 which supports the PTFE membrane 24 and allows gas to pass into the chamber 23. However, any other macro-porous support such as a layer of Vyon or RVC may be used. Purge gas from a source (not shown) flows into the chamber 23 via inlet 30 (FIG. 4) mixes with the generated gas, and exits via outlet 31 in outlet block 32. A controlled concentration of the generated gas in the purge gas is thus produced. The gas concentration may be controlled by varying one or more of the active area of the generating electrode, the current supplied to the electrodes, and the rate of flow of the purge gas.

Figure 1:
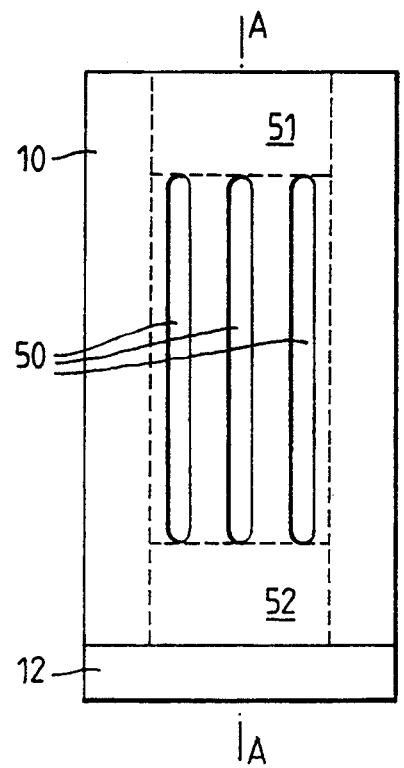
FIG. 1 is a side elevation.

Gas is also evolved at the counter electrode 3 and will collect, to a limited extent, in the electrolyte chamber. In the orientation shown, gas evolved from the counter electrode 3 will collect in positions 40, or 43. In this orientation, pressure compensation is achieved by venting of the gas through the semi-permeable PTFE membranes 41,42. The gas will pass through side vents 50 in side plates 10 or 11, shown in FIG. 1, and also along the interfaces 44,45 between a first portion 51 of the housing 1, and side plates 10 or 11 respectively. Effectively, the bubbles (shown at 40,43) are at all times in contact with the PTFE membranes 41,42 and venting to atmosphere is assured.

If the device is turned by 90° anti-clockwise from the orientation shown in FIG. 2, the gas bubble in the position 40 will pass along the slanting wall 46, round the generating electrode 2 via a gallery 60 (shown in FIG. 4), and will lie along the PTFE membrane 42, venting through side vents 50. The slanting wall 46 ensures that the bubble does not remain on the counter electrode side of the electrode chamber and expose the counter electrode. If the device is turned by slightly less than 90°, and the bubble in the position 40 does not pass along the slanting wall 46, the bubble will enlarge, but not sufficiently to fully expose the counter electrode.

If the device is turned by 180° from the orientation shown in FIG. 2, the gas bubbles in positions 40 and 43 will move so as to lie in a thin layer along a wall 15 defined by the upper face of the base of housing 1 and against the PTFE sealing gasket 6. The counter electrode will not be exposed due to the raised portion of the support 7, which stands out from the wall 15 and surrounds the electrode and gas will vent through side vents 50 in side plates 10 or 11, and also along the interfaces 47,48 between a second portion 52 of the housing 1, and side plates 10 or 11 respectively. Thus, in all orientations, gas build up will not be sufficient to cause high pressure in the electrolyte chamber, or drying out of either the counter or generating electrodes, which would cause a loss of Faraday efficiency, and ultimately an open circuit.

The gap 25 between the generating electrode and gas PTFE membrane 24 must be sufficiently small so as to ensure that substantially no bubbles are formed by the gas there. This ensures that the gas in the electrolyte will diffuse across the gap 25 due to the gaseous concentration gradient, regardless of orientation of the device, ensuring that the gas passes into the purge gas chamber.

In a preferred embodiment, the gas generated at the electrode 2 is chlorine. The electrolyte is an aqueous solution of LiCl, CuCl$_2$ and HCl to pH 1. The generating electrode 2 is formed of titanium with a coating of ruthenium dioxide and is the anode, and the chlorine generating reaction is:

$$2HCl \rightarrow 2H^+ + Cl_2 + 2e$$

Electrodeposition of copper occurs at the counter electrode (cathode) due to the reaction:

$$Cu^{++} + 2e \rightarrow Cu$$

In this case the preferred counter electrode material is titanium.

Alternative cathodic reactions may be employed at the counter electrode, for example hydrogen evolution or oxygen reduction at platinum electrodes:

$$2H^+ + 2e \rightarrow H_2$$

$$O_2 + 4H^+ + 4e \rightarrow 2H_2O$$

In the case of a chlorine generator, the gap 25 (which must be accurately maintained) should be less than approximately 127 micron (about 5 thou) in order to prevent bubble formation, but greater than approximately 76 micron (about 3 thou) in order to maintain Faraday efficiency.

In addition, the generator may be used to produce Hydrogen Sulphide, Hydrogen Cyanide, Hydrogen, Chlorine Dioxide or other gases which may be produced by electrolysis. The electrodes, electrolyte and gap 25 will have to be chosen accordingly.

A carbon filter may be fitted to purge gas inlet 30 in order to remove particulate and gaseous contaminants from the purge gas stream.

The cell is powered by a constant current power supply which can detect a sudden change in cell voltage such as may be caused by a build up of gas in the electrolyte chamber.

Faraday efficiencies of between 97% and 102% have been consistently achieved using a chlorine generator as described.

We claim:

1. Gas generating apparatus comprising an electrochemical cell having gas generating and counter electrodes with an intervening body of electrolyte, whereby current passing between said electrodes causes the generation of gas at said gas generating electrode, the apparatus further comprising a first membrane permeable to gas but substantially impermeable to said electrolyte positioned sufficiently close to said gas generating electrode that gas generated by said gas generating electrode diffuses through said electrolyte and out through said membrane under the influence of a gas concentration gradient, substantially without forming bubbles in the electrolyte and irrespective of the orientation of the apparatus, and wherein said electrochemical cell defines a generally U-shaped electrolyte chamber having a pair of arms connected to a base, said counter electrode extending into one of said arms of the U and the gas generating electrode being positioned at said base of the U.

2. Apparatus according to claim 1, wherein said chamber is defined by walls, and wherein said walls are at least partly formed of a second membrane permeable to gas but substantially impermeable to electrolyte arranged such that gas generated by said counter electrode can vent through said walls.

3. Apparatus according to claim 2, wherein one or both of the first and second membranes comprises porous PTFE.

4. Apparatus according to claim 1, wherein said first membrane is supported by a relatively highly porous support member.

5. Apparatus according to claim 4, wherein said highly porous support member is made from one of Vyon and Reticulated Vitreous Carbon.

6. Apparatus according to claim 1, wherein said chamber is defined by walls including an inner wall which defines said arm of the U containing said counter electrode, said inner wall being angled towards said base of the U so as to encourage the passage of gas into the other arm when the apparatus is tilted.

7. Apparatus according to claim 1, wherein the distance between said first membrane and said gas generating electrode is not less than 70 $\mu$m.

8. Apparatus according to claim 7, wherein the distance between said first membrane and said gas generating electrode (2) is not less than 76 $\mu$m.

9. A calibrating gas generating system comprising gas generating apparatus an electrochemical cell having gas generating and counter electrodes with an intervening body of electrolyte, whereby current passing between said electrodes causes the generation of gas at said gas generating electrode, the apparatus further comprising a first membrane permeable to gas but substantially impermeable to said electrolyte positioned sufficiently close to said gas generating electrode that gas generated by said gas generating electrode diffuses through said electrolyte and out through said membrane under the influence of a gas concentration gradient, substantially without forming bubbles in the electrolyte and irrespective of the orientation of the apparatus, and wherein said electrochemical cell defines a generally U-shaped electrolyte chamber having a pair of arms connected to a base, said counter electrode extending into one of said arms of the U and the gas generating electrode being positioned at said base of the U; and a purge gas chamber into which gas transmitted through said first membrane passes, and in which the gas is mixed with a purge gas.

* * * * *